United States Patent [19]

Copes

[11] 3,940,258
[45] Feb. 24, 1976

[54] METHOD FOR CONTROLLING AQUATIC WEEDS WITH N-PHENYLALKYL-γ-HYDROXYBUTYRAMIDE

[75] Inventor: Joseph P. Copes, Easton, Pa.

[73] Assignee: GAF Corporation, New York, N.Y.

[22] Filed: Jan. 23, 1974

[21] Appl. No.: 435,935

Related U.S. Application Data

[63] Continuation-in-part of Ser. No. 202,595, Nov. 26, 1971, abandoned.

[52] U.S. Cl. .......................... 71/66; 71/67; 71/118; 106/14; 106/287; 106/310; 149/108.8; 149/109.4; 252/50; 260/326.5 J; 260/561 B; 106/15 R; 106/287 R
[51] Int. Cl.² .............................................. A01N 9/00
[58] Field of Search ................................ 71/66, 67

[56] References Cited
UNITED STATES PATENTS

| | | | |
|---|---|---|---|
| 2,935,393 | 5/1960 | Luckenbaugh | 71/66 X |
| 3,236,871 | 2/1966 | Hinman et al. | 71/66 |
| 3,540,875 | 11/1970 | Berger | 71/67 X |

OTHER PUBLICATIONS

Spath et al., Ber. 69B, 2727–2731, (1936).
Reppe, Chemical Abstracts, 50, 16786e.

Primary Examiner—Glennon H. Hollrah
Attorney, Agent, or Firm—Walter C. Kehm

[57] ABSTRACT

Process of employing as herbicides N-phenylalkyl - γ hydroxybutyramide or methyl or halo derivatives thereof wherein the methyl or halo substituent occupies any one of two of the ortho-, meta- and para-positions of the phenyl ring; said compounds having the following formula:

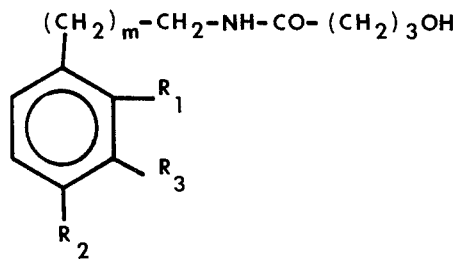

wherein $m$ is 1 or 0 and $R_1$ is hydrogen, methyl, chlorine, or bromine; $R_2$ is hydrogen, methyl or, when $R_1$ is other than hydrogen, $R_2$ can also be chlorine or bromine; and $R_3$ is hydrogen or, when $R_1$ is hydrogen, $R_3$ can also be chlorine or bromine.

The above compounds are useful as plant growth regulating agents particularly as a herbicide or control agents for aquatic weeds.

9 Claims, No Drawings

METHOD FOR CONTROLLING AQUATIC WEEDS WITH N-PHENYLALKYL-Γ-HYDROXYBUTYRAMIDE

This application is a continuation-in-part of Ser. No. 202,595 filed Nov. 26, 1971 now abandoned, the entire disclosure of which is incorporated herein.

This invention relates to a process for using a N-phenylalkyl-γ-hydroxybutyramide and derivatives thereof in the control of aquatic weeds.

The preparation of subject compounds is known from the literature. For example, Spath, E., et al. Ber 69B, 2727-31 (1936) CA 31, 2272$^8$ react γ-hydroxybutyric acid lactone with benzyl amine at a temperature of 215°–220°C. to obtain as the reaction product, N-benzyl-γ-hydroxybutyramide in 42% yield. It is further known from the literature (Reppe, W. CA 50, 16786 ie) that when 214 g. benzyl amine (b.p. 187°C.) are reacted with 172 g. γ-butyrolactone (b.p. 204°C.) for 8 hours, there is obtained only 184 g. of reaction product amounting to a yield of 47.6% of the theoretical. After recrystallization of this latter reaction product from ethylacetate, the compound recovered has a melting point of 70°–72°C.

It is an object of the invention to provide a process for employing a N-benzyl-γ-hydroxybutyramide and derivatives thereof in the control of aquatic weeds.

Another object of the invention is to provide a process for the use of a N-benzyl-γ-hydroxybutyramide and derivatives thereof as thickening agents for protective coatings including oils, greases and paints.

Still another object of the invention is to provide a low temperature process for the economical preparation of N-benzyl-γ-hydroxybutyramide and derivatives as superior and inexpensive herbicides.

Yet another object of the invention is to provide compositions containing a N-benzyl-γ-hydroxybutyramide as active ingredient which are suitable as plant growth regulating agents and are particularly adapted for regulating growth of aquatic weeds.

Those and other objects and advantages of the invention will become apparent from consideration of the following disclosure.

In accordance with the invention, it is now surprisingly found that the N-phenylalkyl-γ-hydroxybutyramide and its methyl and halo derivatives can be synthesized in substantial quantitative yield at a temperature of only 150°C. in a reaction time amount to only a few minutes according to the following reaction scheme:

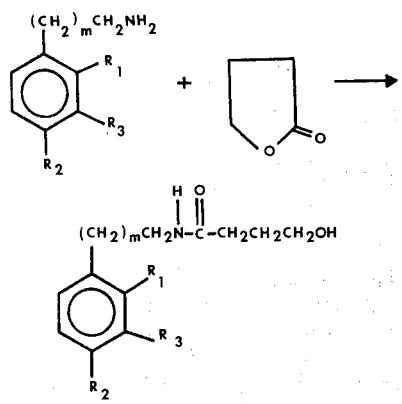

wherein $m$, $R_1$, $R_2$ and $R_3$ are as designated above.

The reaction of the invention is accordingly effected at considerably lower temperatures than have heretofore been employed, i.e., from about 30°, up to 200°C. It has now been discovered that, when reaction is effected at 250°–300°C., the N-benzyl-2-pyrrolidone is predominantly formed instead of N-benzyl-γ-hydroxybutyramide, and that even between 200° and 250°C., substantial quantities of the benzylpyrrolidone compound is obtained. The N-benzyl-2-pyrrolidone is innocuous to aquatic weeds and is, therefore, considered a poison in aquatic herbicidal compositions, since it dilutes the active species and shortens its effective life. A reaction time amounting to minutes for N-benzyl-γ-hydroxybutyramide and the above derivatives rather than hours, as was heretofore believed necessary by the art, has also been found most effective at temperatures between 100° and 180°C.

Additional advantages of the invention lie in that no enclosed equipment is required, condensers are not necessary, considerable energy in the form of heat is saved and the equipment involved is not committed for long periods of time. Further, the process of the invention is adapted to both batch and continuous operation. Continuous operation can be carried out, for example, by proportionately pumping the liquid benzyl amine and the liquid γ-butyrolactone through a heated reactor for the required residence time. The molten product obtained can be fed into storage vessels or shipping containers wherein it is allowed to solidify.

In order to better disclose the process for preparing the N-benzyl-γ-hydroxybutyramides, the following examples are furnished. It is to be clearly understood that these examples are illustrative only of the improved process for making subject compounds and that any other process resulting in these products can be employed to obtain the active herbicides of the present invention.

EXAMPLE 1

There were weighed into a beaker, 21.4 g. (0.2 mol) benzyl amine and 17.2 g (0.2 mol) γ-hydroxybutyric acid lactone. The resultant mixture was heated to 150°C. over a flame for 15 minutes and allowed to cool. The product which thereby formed in 100% yield was a hard, waxy, white solid which melted at 70°–72°C. without recrystallization. The N-benzyl-γ-hydroxybutyramide product was identified by its IR and NMR spectra.

EXAMPLE 2

Example 1 was repeated but using 86 g. γ-butyrolactone and 107 g. benzyl amine. This mixture was heated to 150°C., maintained at this temperature for 10 minutes and then poured onto a slab. The product on cooling, obtained in 100% yield, formed a substance identical to that obtained in Example 1. The above procedure illustrates the process of the invention carried out on a larger scale than that described in the preceding example.

EXAMPLE 3

A portion of the product prepared in Example 1 was heated over a short time to 250°C. and then chilled without any observed alteration of material. The foregoing substantiates the wide range of the temperature stability of the product and the fact that subject composition can be economically produced in comparable yield and higher purity without resorting to high temperatures and extended reaction time.

A temperature range of 30°–200°C. and a reaction time ranging from one minute or less to slightly longer periods can be advantageously used in carrying out the process of the invention. The reaction takes place quite rapidly at 100°C. and is essentially instantaneous at higher temperatures. The use of temperatures above 250°C. for periods above 15 minutes is to be avoided as this results in loss of selectivity by the formation of significant amounts of undesirable side reactions which produce the corresponding alkyl butyramide and methyl butyl ester and N-benzyl-2-pyrrolidone. Further, the reaction can be carried out in an appropriate solvent such as water acetone, acetic acid as well as many others, if the product to be recovered is desired in liquid form. In presence of some solvents, it is desireable to carry out the reaction in an enclosed reactor capable of withstanding low pressures.

EXAMPLE 4

There were weighed into a beaker 7.08 g. (.05 mol) p-chlorobenzylamine and 4.3 g. (.05 mol) γ-hydroxybutyric acid lactone. The resultant mixture was heated to 167°C. over a flame for 1 hour and allowed to cool. The product which thereby formed in 100% yield was a hard, waxy, white solid. The N-(p-chlorobenzyl)-γ-hydroxybutyramide product was identified by its IR and NMR spectra.

EXAMPLE 5

There were weighed into a beaker 5.0 g. m-chlorobenzylamine and 3.04 g. γ-hydroxybutyric acid lactone. The resultant mixutre was heated to 166°C. over a flame for 1 hour and allowed to cool. The product which thereby formed in 100% yield was a liquid which did not immediately freeze when cool. The N-(m-chlorobenzyl)-γ-hydroxybutyramide product was identified by its IR spectrum.

EXAMPLE 6

There were weighed into a beaker 8.8 g. 2,4-dichlorobenzylamine and 4.3 g. γ-hydroxybutyric acid lactone. The resultant mixture was heated to 170°C. over a flame for 2 hours and allowed to cool. The product which thereby formed in 97% yield slowly froze to a pale yellow solid on a period of 5 weeks. The N-(o-,p-dichlorobenzyl)-γ-hydroxybutyramide product was identified by its IR and NMR spectra.

EXAMPLE 7

There were weighed into a beaker 6.1 g. 4-methylbenzylamine and 4.3 g. γ-hydroxybutyric acid lactone. The resultant mixture was heated to 160°C. over a flame for 1 hour and allowed to cool. The product which thereby formed in 100% yield was a hard, waxy, white solid. The N-(p-methylbenzyl)-γ-hydroxybutyramide product was identified by its IR and NMR spectra.

EXAMPLE 8

There were weighed into a beaker 8.8 g. 3,4-dichlorobenzylamine and 4.3 g. γ-hydroxybutyric acid lactone. The resultant mixture was heated to 165°C. over a flame for 1 hour and allowed to cool. The product which thereby formed in 100% yield was a white solid. The N-(m-p-dichlorobenzyl)-γ-hydroxybutyramide product was identified by its IR and NMR spectra.

EXAMPLE 9

There were weighed into an Erlenmeyer flask 64.4 g. phenethyl amine and 45.8 g. γ-hydroxybutyric acid lactone. The resultant mixture was heated to 190°C. over a flame for 1 hour and allowed to cool. The product which thereby formed in 100% yield was a hard, waxy, white solid. The N-phenethylbutyramide product was identified by its IR spectrum.

EXAMPLE 10

There were weighed into a beaker 4.9 g. α-1-aminopseudocumene and 3.1 g. γ-hydroxybutyric acid lactone. The resultant mixture was heated to 167°C. over a flame for 1 hour and allowed to cool. The product which thereby formed in 100% yield was a white solid. The N-(2,4-dimethylbenzyl)-4-hydroxybutyramide product was identified by its IR and NMR spectra.

The following hydroxybutyramides were prepared for the purpose of comparing herbicidal properties with those of the above compounds.

EXAMPLE 11

There were weighed into a beaker 4.9 g. α-2-aminopseudocumene and 3.1 g. γ-hydroxybutyric acid lactone. The resultant mixture was heated to 164°C. over a flame for 1 hour and allowed to cool. The white solid product which thereby formed in 100% yield. The N-(2,5-dimethylbenzyl)-4-hydroxybutyramide product was identified by its IR and NMR spectra.

EXAMPLE 12

There were weighed into a beaker 7.8 g. p-chlorophenethylamine and 4.3 g. γ-hydroxybutyric acid lactone. The resultant mixture was heated to 165°C. over a flame for 1 hour and allowed to cool. The light yellow solid product which thereby formed in 100% yield. The N-(p-chlorophenethyl)-γ-hydroxybutyramide product was identified by its IR and NMR spectra.

EXAMPLE 13

There were weighed into a beaker 6.8 g. m-xylylenediamine and 8.6 g. γ-hydroxybutyric acid lactone. The resultant mixture was heated to 180°C. over a flame for 1 hour and allowed to cool. The product slowly froze during 6 weeks in 100% yield. The N,N'-m-xylylenebis (γ-hydroxybutyramide) product was identified by its IR and NMR spectra.

EXAMPLE 14

There were weighed into a beaker 11.3 g. hexahydrobenzylamine and 8.6 g. γ-hydroxybutyric acid lactone. The resultant mixture was heated to 175°C. over a flame for 1 hour and allowed to cool. The colorless liquid product was thereby formed in 100% yield. The N-cyclohexanemethyl-γ-hydroxybutyramide product was identified by its IR and NMR spectra.

EXAMPLE 15

There were weighed into a beaker 6.9 g. p-methoxybenzylamine and 4.3 g. γ-hydroxybutyric acid lactone. The resultant mixture was heated in a 160°C. oil bath for 1 hour and allowed to cool. The white solid product which thereby formed in 100% yield. The N-(p-methoxybenzyl)-γ-hydroxybutyramide product was identified by its IR and NMR spectra.

EXAMPLE 16

There were weighed into a beaker 7.2 g. 1,4-bis-(aminomethyl)cyclohexane and 8.6 g. γ-hydroxybutyric acid lactone. The resultant mixture was heated to 170°C. over a flame for 1 hour and allowed to cool. The waxy solid product which thereby formed in 100% yield. The N,N'-(1,4-cyclohexanedimethylene)-bis(4-hydroxybutyramide) product was identified by its IR and NMR spectra.

EXAMPLE 17

There were weighed into a beaker 100 g. hydrazine hydrate (a 100% excess) and 86 g. γ-hydroxybutyric acid lactone added gradually with cooling and stirring. The reaction took place at a maximum temperature of about 35°C. When cooled, 97 grams of large white crystals were obtained in 82% yield. The product had a melting point of 92° – 95°C. Identification was as follows:
Calculated for: $C_4H_{10}N_2O_2$, C 40.6, H 8.53, N 23.8
Found: C 40.61, H 8.54, N 23.39, 23.35
The product obtained was 4-hydroxybutyric acid hydrazide.

EXAMPLE 18

There were weighed into a beaker 14.6 g. butylamine and 17.2 g. γ-hydroxybutyric acid lactone. The resultant mixture was heated to 130°C. over a flame for 1 hour and allowed to cool. The N-butyl-γ-hydroxybutyramide product was identified by its IR spectrum.

EXAMPLE 19

There were weighed into a beaker 37 g. Armeen C D and 17.2 g. γ-hydroxybutyric acid lactone. The resultant mixture was heated to 100°C. over a flame for 1 hour and allowed to cool. The solid product, which thereby formed in 97% yield, was a very pale amber waxy solid identified as N-dodecyl-γ-hydroxybutyramide by IR spectrum.

EXAMPLE 20

Into a flask were weighed 442 grams (7.54 mols) hydrazine hydrate and 2.41 g. (7.54 mols) γ-butyrolactam. After being allowed to stand several days ambient temperature, crystals were formed. The charge was distilled to a pot temperature of 161°C. whereupon there was obtained 198 grams of water (theoretical = 201 grams) and product 4,4'-dihydroxybibutyramide which was identified by IR spectrum.

The N-benzyl-γ-hydroxybutyramide products produced in accordance with the invention or by any other process are useful as thickening agents for various liquids and, in particular, for lubricating oils and greases as well as paints; as intermediates for use in further chemical reactions including the preparation of biologically active materials such as N-substituted-2-pyrrolidones; and as aquatic herbicides effective against potamogeton, elodea, salvinia and duckweed, etc. Other uses for these materials are as components of rust-preventive compositions, drying oils and incendiary compositions.

In regard to the use of the N-benzyl-γ-hydroxybutyramides as thickening agents, they can be added directly in a concentration between 0.1 and 10% by volume to a paint or oil formulation to provide a thickened, dipless paint or a lubricating grease.

In particular, the compounds of the present invention are superior aquatic herbicides which possesses high activity and which deposit none of the halogenated residue resulting from use of other commonly employed herbicidal compositions. Consequently, large areas can be treated with the present compound while avoiding buildup of ecologically deleterious by-products such as are associated with the use of 2,4-D* which deposits chlorinated hydrocarbon residues harmful to aquatic, animal and bird life in the areas where applied and in substantially extensive surrounding areas.

* 2,4-dichlorophenoxy acetic acid commercially available and usually obtained in admixture with 2,4,5-trichlorophenoxy acetic form chlorodibenzodioxin by-products.

The compounds of the present invention are usually applied to the plant situs, preferably an aquatic plant situs, in a concentration of between 0.1 to 25 lbs./acre and may be employed in the form of water soluble solid granules or dust compositions which can be scattered on the surface of the ground or water over the area intended for treatment or as an aqueous solution in vehicles including water, alcohol, kerosine, acetone, dimethyl sulfoxide, etc. Solids with which the present compound can be mixed include talc, clay, diatomaceous earth, pulverized oak leaves, vermiculite, kaolin, pumice, bentonite, fuller's earth, asbestos, chalk, cross-linked polyvinylpyrrolidone, etc. Generally, the concentration of the compound in the carrier is between 0.05 and about 25% by volume; however, the effective amount for the particular application an be determined by the user and the species to be destroyed.

The present composition can be applied to the situs on either a pre-emergence or post-emergence basis as illustrated by the following examples which are not to be construed as limiting to the scope of the invention but rather as being illustrative and representative of the applications as herbicides.

Stated in other terms, the effective concentration of the present N-benzyl-γ-hydroxybutyramides in a suitable carrier is between about 1 ppm and about 50 ppm, preferably between about 3ppm and about 15 ppm, amd most preferably between 4 and 8 ppm.

In the formulation of the herbicidal composition, wetting agents such as nonionic surfactants, such as polyoxyethylated alkyl phenols, neutral ethylene oxide derivatives, may be employed in a concentration between about 1 and about 5% to provide contact with the members of certain plants which extend out of the water, such as duckweed. Further, diluents and inert carriers may be optionally employed in order to apply the present agents which are highly potent at such a low dose rate without overdose and waste. The agents may be treated with binders such as for example, emulsified raw linseed oil, natural oils, fats, waxes, drying oil, poly vinyl alcohol, polyvinylpyrrolidone in a concentration between about 1 and about 5% to prevent rapid run-off, i.e., to maintain longer contact. Gelling agents such as starches, sugar and cross-linked polymers or polyvinyl pyrrolidone may also be employed as multipurpose addition agents to dilute and to give body to the product composition when desired.

The following tabulation provides representative hydroxybutyramides prepared with butyrolactone as set forth above and reports upon testing the compounds as 5ppm solutions on various aquatic weeds.

The general procedure for treating comprises adding a water solution of 5ppm of the individual hydroxybutyramide compound into a glass vessel maintained with illumination, nutrients, and temperature suitable to support the aquatic plant life tested. The suitability of the aqueous medium in the absence of added hydroxybutyramide was tested by immersing each plant in the medium and allowing it to remain in said medium for 3 months, at which time the control was terminated. No harmful effect on any of the plants so tested in the absence of herbicide was evidenced.

The results reported in the following table were obtained after the plant had been immersed for 3 weeks in the hydroxybutyramide injected aqueous medium.

Table 1

| Formula - name of Hydroxybutyramide at 5 ppm | Weed Tested - % Destroyed (Kill) | | | | |
|---|---|---|---|---|---|
| | Potamogeton | Algae | Elodea | Solvenia | Duckweed |
| N-benzyl-4-hydroxybutyramide | 100 | 100 | 100 | 100 | 100 |
| 4-hydroxy-N-(p-methylbenzyl)butyramide | 60 | N.T. | 100 | 90 | N.T.* |
| N-(p-chlorobenzyl)-4-hydroxybutyramide | 90 | N.T. | 100 | 100 | 60 |
| N-(m-chlorobenzyl)-4-hydroxybutyramide | 100 | N.T. | 60 | 30 | 30 |
| N-(2,4-dichlorobenzyl)-4-hydroxybutyramide | N.T. | N.T. | 90 | N.T. | 30 |
| N-(3,4-dichlorobenzyl)-4-hydroxybutyramide | 30 | N.T. | 90 | 30 | 30 |

Table 1-continued

| Formula - name of Hydroxybutyramide at 5 ppm | Weed Tested - % Destroyed (Kill) | | | | |
|---|---|---|---|---|---|
| | Potamogeton | Algae | Elodea | Solvenia | Duckweed |

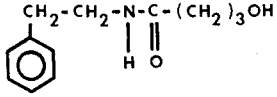

4-hydroxy-N-phenethyl butyramide | N.T. | N.T. | 90 | N.T. | 60

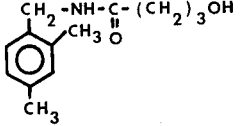

N-(2,4-dimethylbenzyl)-4-hydroxybutyramide | 100 | N.T. | 60 | N.T. | 60

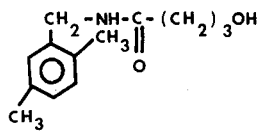

N-(2,5-dimethylbenzyl)-4-hydroxybutyramide | 0 | 0 | 0 | 0 | 0

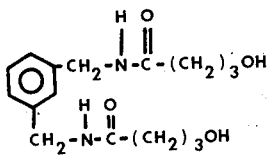

N,N'-m-xylylenebis(4-hydroxybutyramide) | N.T. | 30 | N.T. | N.T. | N.T

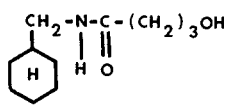

N-cyclohexanemethyl-4-hydroxybutyramide | 0 | 0 | 0 | 0 | 0

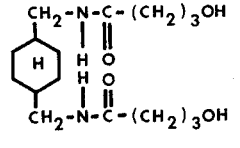

N,N'-(1,4-cyclohexanedimethylene) bis-(4-hydroxybutyramide) | 0 | 0 | 0 | 0 | 0

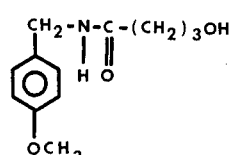

N-(p-methoxybenzyl)-4-hydroxybutyramide | 30 | N.T. | 30 | N.T. | N.T.

Table 1-continued

| Formula - name of Hydroxybutyramide at 5 ppm | Weed Tested - % Destroyed (Kill) | | | | |
|---|---|---|---|---|---|
| | Potamogeton | Algae | Elodea | Solvenia | Duckweed |
| NH—CO—(CH$_2$)$_3$OH | | | | | |
| NH—CO—(CH$_2$)$_3$OH | | | | | |
| Bibutyramide-4,4'-dihydroxy | 0 | 0 | 0 | 0 | 0 |
| CH$_3$(CH$_2$)$_3$—NH—CO—(CH$_2$)$_3$OH | | | | | |
| N-butyl-4-hydroxybutyramide | 0 | 0 | 0 | 0 | 0 |
| CH$_3$(CH$_2$)$_{11}$—NH—CO—(CH$_2$)$_3$OH | | | | | |
| N-dodecyl-4-hydroxybutyramide | 0 | 0 | 0 | 0 | 0 |

*Not Tested

In the above table, there are many instances where the particular compound was not tested against algae. Since of the plant species tested, algae are most easily killed, it was assumed that where the compound possessed ability to kill other plant species its toxicity to algae would be at least as great as that demonstrated for potamogeton or elodea, whichever is higher. Conversely, where the compound displayed only 30% toxicity toward algae, it would be expected to be substantially innocuous toward other plant species and was not further tested. Since duckweed was found to be the most resistant to herbicides, in cases where the compound had only 30% toxicity to both potamogeton and elodea it was expected to be relatively innocuous toward duckweed and was, therefore, not tested further.

What is claimed is:

1. The method of controlling the growth of aquatic weeds which comprises applying to the site where said growth is to be controlled, an effective amount of an herbicidal composition comprising as the active component, an N-phenylakyl-2-hydroxybutyramide having the following formula:

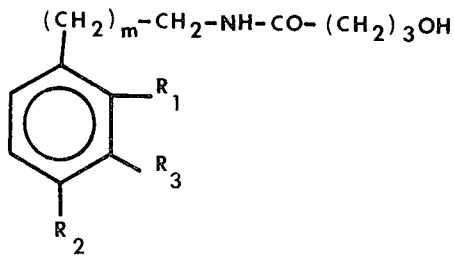

wherein $m$ is 1 or 0; at least one of $R_1$ and $R_3$ is hydrogen and the other is hydrogen, methyl, chlorine or bromine, and $R_2$ is hydrogen, methyl, chlorine or bromine.

2. The process of claim 1 wherein the benzylhydroxybutyramide is unsubstituted or is substituted in the para position.

3. The process of claim 1 wherein an inert carrier is employed with the benzylhydroxybutyramide and the concentration of the benzylhydroxybutyramide is between about 0.05 and about 25% by volume with respect to the inert carrier.

4. The process of claim 3 wherein the composition additionally contains at least one additive selected from the group comprising a wetting agent, a binder and a gelling agent.

5. The process of claim 3 wherein the carrier is selected from the group comprising diatomaceous earth, talc, vermiculite, kaolin, pumice, bentonite, fuller's earth, asbestos, chalk, cross-linked polyvinylpyrrolidone, alcohol, kerosine, acetone, dimethyl sulfoxide and water.

6. The process of claim 4 wherein the composition contains a non-ionic surfactant as a wetting agent.

7. The process of claim 4 wherein the composition contains a binder.

8. The process of claim 4 wherein the composition contains a gelling agent.

9. The method of claim 1 wherein 1 to 50 parts per million of the benzylhydroxybutyramide is applied to the plant situs.

* * * * *